US012740631B2

(12) United States Patent
Lu

(10) Patent No.: US 12,740,631 B2
(45) Date of Patent: Sep. 22, 2026

(54) COMPOUND FACIAL MASK

(71) Applicant: DARWIN PRECISIONS CORPORATION, Hsinchu County (TW)

(72) Inventor: Chi Ying Lu, Hsinchu County (TW)

(73) Assignee: DARWIN PRECISIONS CORPORATION, Hsinchu County (TW)

( * ) Notice: Subject to any disclaimer, the term of this patent is extended or adjusted under 35 U.S.C. 154(b) by 193 days.

(21) Appl. No.: 18/444,798

(22) Filed: Feb. 19, 2024

(65) Prior Publication Data

US 2024/0374015 A1 Nov. 14, 2024

(30) Foreign Application Priority Data

May 8, 2023 (TW) ................................ 112116988

(51) Int. Cl.

*A45D 44/00* (2006.01)
*A61K 8/02* (2006.01)
*A61M 37/00* (2006.01)

(52) U.S. Cl.

CPC .......... *A45D 44/002* (2013.01); *A61K 8/0212* (2013.01); *A61M 37/0015* (2013.01); *A61M 2037/0061* (2013.01)

(58) Field of Classification Search

CPC ............... A45D 44/002; A61K 8/0212; A61M 37/0015; A61M 2037/0061; A61M 2037/0007; A61M 2037/0023; A61Q 19/00; A61N 1/0502; A61N 1/327; A61N 1/328; A61N 1/36

See application file for complete search history.

(56) References Cited

FOREIGN PATENT DOCUMENTS

| | | | |
|---|---|---|---|
| CN | 106310515 A | * | 1/2017 |
| CN | 106310515 B | | 10/2018 |
| CN | 109562261 A | | 4/2019 |
| CN | 109718465 B | * | 1/2022 |
| CN | 109562261 B | * | 2/2023 |

* cited by examiner

*Primary Examiner* — Robert A Wax
*Assistant Examiner* — Kimberly Barber

(57) ABSTRACT

A compound facial mask includes a flexible body, a discharge pattern, and a microneedle portion. The discharge pattern is positioned on the surface of the flexible body. The discharge pattern includes two metals, and the two metals have different redox potentials. The microneedle portion is positioned on the surface of the flexible body, prepared from a material different from the discharge pattern and provided with a plurality of conductive microneedles. By adopting the compound facial mask, absorption by the skin of a user can be promoted, and the absorption rate of ingredients in a liquid used in cooperation with the compound facial mask is increased.

12 Claims, 5 Drawing Sheets

COMPOUND FACIAL MASK

FIELD OF THE INVENTION

The present invention relates to a facial mask, and more particularly to a facial mask using an electric current.

BACKGROUND OF THE INVENTION

Skin is the first line of defense of the human body against external harmful substances or microorganisms and is provided with stratum corneum on the outermost layer, which can prevent the microorganisms from entering the human body, prevent dehydration of cells and provide physical protection. However, the situation also causes the skin not easily to absorb beneficial ingredients in drugs or beauty liquids.

In the current field of medical cosmetology, a micro-current dressing capable of using an electric current generated by an external power source to stimulate cells and promote absorption of the ingredients in the beauty liquids by the skin is provided. According to electric current generation methods, facial mask products containing micro-current dressing can be mainly divided into two types: one type using potential differences generated by different materials to realize automatic power generation and another type using additional power supply devices to generate potential differences. However, as micro-currents are still mainly generated on facial masks, the micro-currents are conducted on the surface skin of a user and are difficult to be conducted on deep skin.

SUMMARY OF THE INVENTION

The present invention provides a facial mask. The facial mask can increase the absorption rate of active ingredients of a beauty liquid, has better effects, and solves the problem that active ingredients of beauty liquids are not easily absorbed by the skin.

In order to achieve the above advantages, one embodiment of the present invention provides a compound facial mask. The compound facial mask includes a flexible body, a discharge pattern, and a microneedle portion. The discharge pattern is positioned on a surface of the flexible body, the discharge pattern includes two metals, and the two metals have different redox potentials. The microneedle portion is positioned on the surface, and the microneedle portion is prepared from a material different from the discharge pattern and provided with a plurality of conductive microneedles.

In one embodiment of the present invention, the discharge pattern is formed by printing with a coating, and the coating includes two metal particles having different redox potentials.

In one embodiment of the present invention, the discharge pattern is provided with a first pattern portion and a second pattern portion, the first pattern portion and the second pattern portion are separated from each other, and the first pattern portion and the second pattern portion include metal particles having different redox potentials.

In one embodiment of the present invention, the discharge pattern includes at least one first metal line and at least one second metal line. The first metal line is positioned on the flexible body to form the first pattern portion. The second metal line is positioned on the flexible body to form the second pattern portion. The at least one second metal line and the at least one first metal line have different redox potentials and are interlaced and spaced with each other.

In one embodiment of the present invention, the microneedle portion includes a microneedle patch capable of being separated from the flexible body by assembly and disassembly.

In one embodiment of the present invention, the conductive microneedles are insoluble microneedles or soluble microneedles.

In one embodiment of the present invention, the conductive microneedles include cosmetic ingredients.

In one embodiment of the present invention, the compound facial mask further includes a conductive pattern. The conductive pattern covers a surface on one side of the flexible body and is positioned between the flexible body and the discharge pattern.

In one embodiment of the present invention, the surface is provided with at least one first-setting area and at least one second-setting area. The microneedle portion is positioned in the first-setting area, and the discharge pattern is positioned in the second-setting area.

In one embodiment of the present invention, the surface is further provided with a third setting area. The microneedle portion and the discharge pattern are further positioned in the third setting area, and the discharge pattern is positioned between the microneedle portion and the flexible body.

In conclusion, as the compound facial mask of the present invention is provided with a discharge pattern and a microneedle portion at the same time, the absorption rate of active ingredients absorbed by the skin can be increased in two different ways including the discharge pattern for generating a micro-current acting on the skin and the microneedle portion for penetrating into the stratum corneum of the skin. Moreover, the conductive microneedle portion can be used as an electrode for penetrating into the skin to make an electric current conducted to the deeper skin, thereby achieving better effects. The problem that active ingredients of beauty liquids are not easily absorbed by the skin is solved.

Other objectives, features, and advantages of the invention will be further understood from the further technological features disclosed by the embodiments of the invention wherein there are shown and described preferred embodiments of this invention, simply by way of illustration of modes best suited to carry out the invention.

DETAILED DESCRIPTION OF PREFERRED EMBODIMENTS

Figure 1:
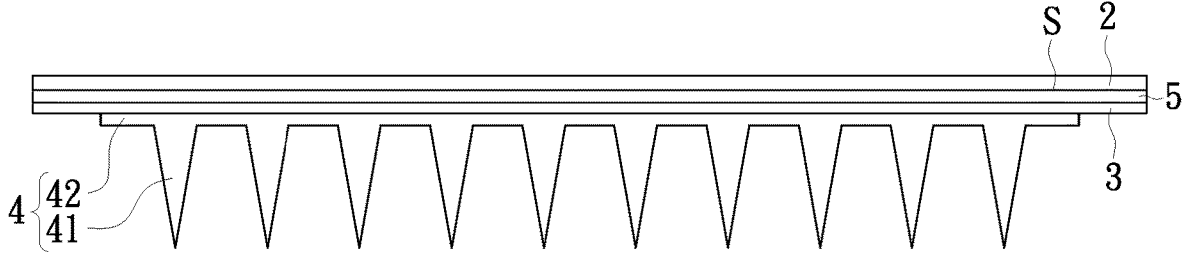
FIG. 1 is a structural schematic diagram of a compound facial mask in one embodiment of the present invention.

Terms used in the description of the embodiments of the present invention, for example, orientation or position relation such as "above" and "below" are described according to the orientation or position relation shown in the drawings. The above terms are used for facilitating the description of the present invention rather than limiting the present invention, i.e., indicating or implying that the mentioned elements have to have specific orientations and be configured in the specific orientations. In addition, terms such as "first" and "second" involved in the description or claims are merely used for naming the elements or distinguishing different embodiments or ranges rather than limiting the upper limit or lower limit of the quantity of the elements.

Figure 2:
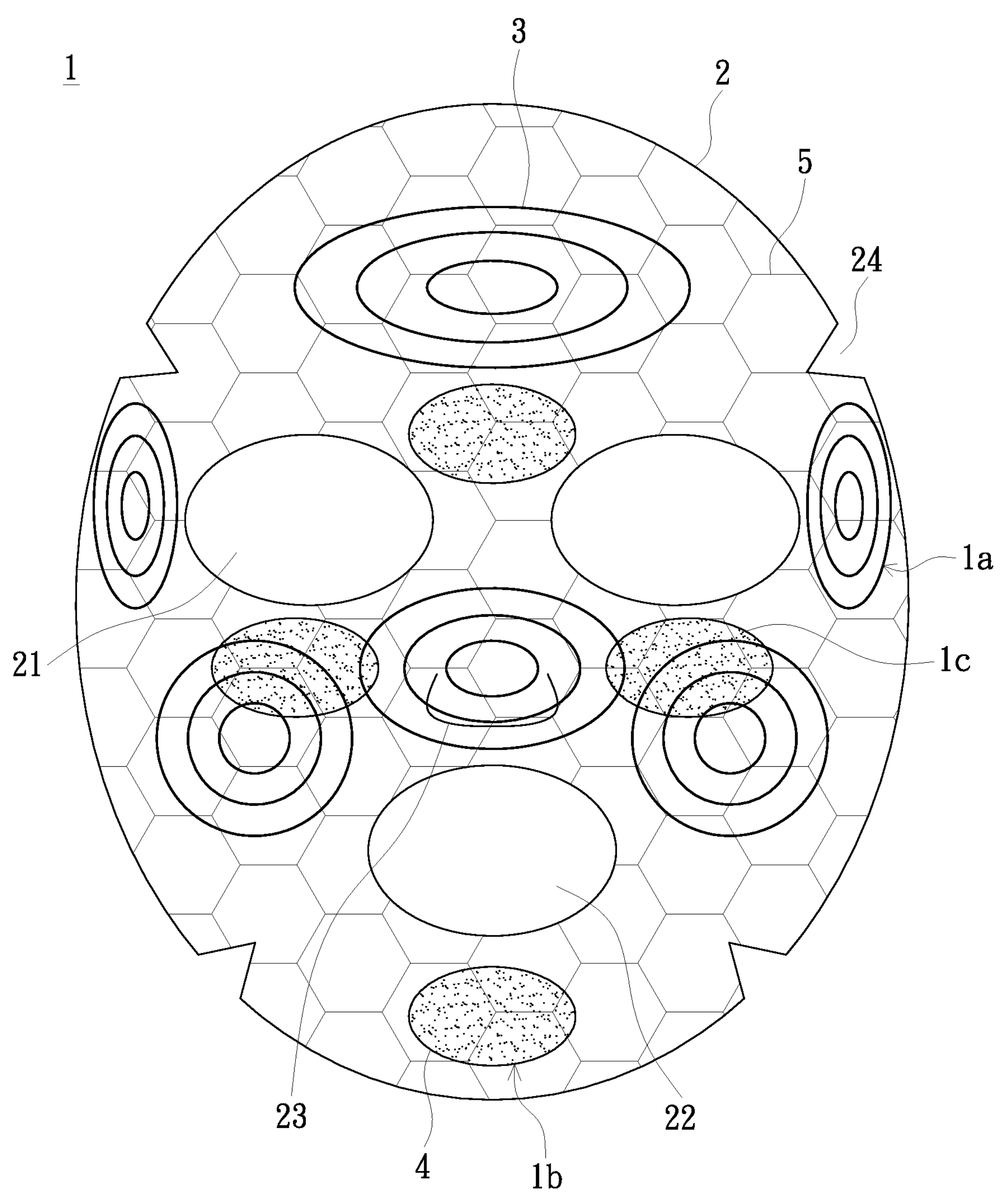
FIG. 2 is a schematic diagram of a front view of a compound facial mask in one embodiment of the present invention.

FIG. 1 is a structural schematic diagram of a compound facial mask in one embodiment of the present invention. FIG. 2 is a schematic diagram of a front view of a compound facial mask in one embodiment of the present invention. As shown in FIG. 1 and FIG. 2, the compound facial mask 1 provided in the present embodiment includes a flexible body 2, a discharge pattern 3, and a microneedle portion 4. The discharge pattern 3 is positioned on the surface of the flexible body 2. The discharge pattern 3 includes two metals, and the two metals have different redox potentials. For example, the discharge pattern 3 is specifically formed by printing with a coating including two metal particles; however, the specific modality is not limited thereto (see subsequent descriptions for details). The microneedle portion 4 is positioned on the surface. The microneedle portion 4 is prepared from a material different from the discharge pattern 3 and has a plurality of conductive microneedles 41 (see FIG. 1).

As shown in FIG. 2, in the present embodiment, the flexible body 2 has, for example, an eye-opening 21 corresponding to the eyes of a user, a mouth-opening 22 corresponding to the mouth of the user, and an incision 23 corresponding to the nose position of the user. In addition, in the present embodiment, an edge of the flexible body 2, for example, is also provided with a notch 24, which can be deformed to better fit the skin of a user when attached to the face of the user. The design for the flexible body 2 to correspond to the face shape of a user is not limited to the above contents and may be set according to demands.

Please refer to FIG. 1 and FIG. 2. In the present embodiment, the compound facial mask 1 further includes a conductive pattern 5. The conductive pattern 5 covers a surface on one side of the flexible body 2 and is positioned, for example, between the flexible body 2 and the discharge pattern 3. The conductive pattern 5 is suitable for guiding a micro-current generated by the discharge pattern 3 to other areas on the compound facial mask 1 to cooperate with the discharge pattern 3 and thereby promote an action effect of the micro-current on the human body.

Figure 3:
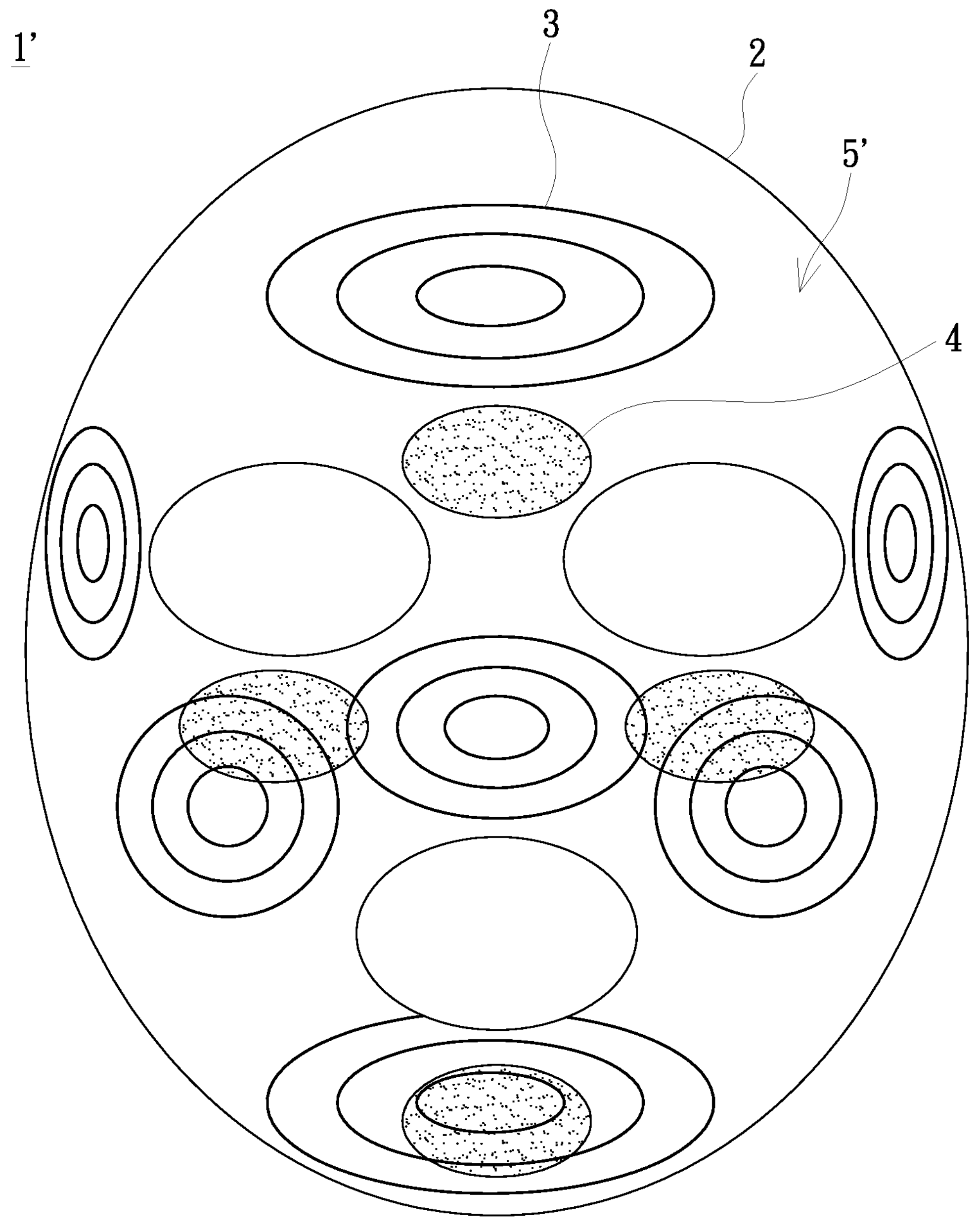
FIG. 3 is a schematic diagram of a front view of a compound facial mask in another embodiment of the present invention.

As shown in FIG. 2, the conductive pattern 5 is, for example, mesh-shaped, and specifically is, for example, hexagonal grid-shaped. The material of the conductive pattern 5 is, for example, graphene ink or a conductive fiber (metal wire); however, the material is not limited thereto. According to the aforementioned materials, it can be seen that the conductive pattern 5 does not have the effect of generating an electric current. In the embodiment as shown in FIG. 3, the conductive pattern 5' on the compound facial mask 1' may be changed into a layer that can completely cover the surface of the flexible body 2.

Please refer again to FIG. 1 and FIG. 2. The compound facial mask 1 is used, for example, in cooperation with a liquid (not shown in the figure), and the liquid is used as an electrolyte required for the discharge pattern 3 and includes, for example, ingredients intended to be absorbed by the skin. However, the ingredients are not limited thereto. In the present embodiment, the flexible body 2 is, for example, made of a non-woven fabric and is suitable for storing the liquid during use and keeping the liquid in a desired position covering the skin of a user.

During use, when the discharge pattern 3 gets in contact with the liquid, the two metals having different redox potentials in the discharge pattern 3 can cooperate with the electrolyte in the liquid to undergo a redox reaction so as to generate an electric current. The two metals are, for example, two different materials optionally selected from gold, silver, copper, iron, chromium, aluminum, tin, lead, zinc, sodium, calcium, and other metals. However, the type of the metals is not limited thereto.

As shown in FIG. 2, in the present embodiment, a surface of the compound facial mask 1 is provided with, for example, a plurality of first-setting areas 1*a* and a plurality of second-setting areas 1*b*. The discharge pattern 3 is positioned in the first-setting area 1*a*, and the microneedle portion 4 is positioned in the second-setting area 1*b*. The specific positions of the first-setting areas 1*a* and the second-setting areas 1*b* are not particularly limited and may be set or changed according to demands. Specifically, the first-setting area 1*a* and the second-setting area 1*b* may be set on positions, corresponding to wrinkled parts around the eyes or the forehead part, on the compound facial mask 1.

In the present embodiment, the discharge pattern 3 is, for example, formed on the flexible body 2 by direct printing during manufacturing. The microneedle portion 4 is, for example, a microneedle patch capable of separating from the flexible body 2 during assembly and disassembly. In particular, the microneedle portion 4 is provided with conductive microneedles 41 and a substrate sheet 42. In another embodiment, the microneedle portion 4 may include a plurality of conductive microneedles 41 directly formed on the flexible body 2 and may not include a substrate sheet 42. The forming method of the microneedle portion 4 may be determined according to the detailed type of the microneedle portion 4 (see the following descriptions for details). In the embodiment where the microneedle portion 4 is a microneedle patch, the microneedle patch may be, for example, manufactured separately from the flexible body 2 and then combined with the flexible body 2 before use. The combination way includes, for example, bonding by a conductive back adhesive on the microneedle portion 4. However, the combination way is not limited thereto.

As shown in FIG. 2, in the present embodiment, the surface of the compound facial mask 1 is further provided with a third setting area 1*c*, and the microneedle portion 4 and the discharge pattern 3 are both positioned in the third setting area 1*c*. In the present embodiment, the discharge pattern 3 is, for example, positioned between the microneedle portion 4 and the flexible body 2. In other words, the microneedle portion 4 is, for example, positioned closest to the skin to prevent the needle tips of the microneedle portion 4 from being damaged during the production of the discharge pattern 3. However, the present invention is not limited thereto.

In different embodiments of the present invention, structures such as the discharge pattern 3, the microneedle portion 4, and the conductive pattern 5 (when provided) that are connected to the flexible body 2 may be superimposed in a layering manner. Specifically, for example, in the third area 1*c* in FIG. 2, the discharge pattern 3, the microneedle portion 4, and the conductive pattern 5 may be superimposed in a manner as shown in FIG. 1. In the first area 1*a* in FIG. 2, superposition may be performed in a manner similar to that in FIG. 1 without having the microneedle portion 4 in FIG.

1. In the second area 1*b* in FIG. 2, superposition may be performed in a manner similar to that in FIG. 1 without having the discharge pattern 3 in FIG. 1 so that the conductive layer 5 and the microneedle portion 4 are superimposed by direct contact. The above structures can be set according to the demands of the compound facial mask 1 in production to change the relative positions.

Figures 4A, 4B:
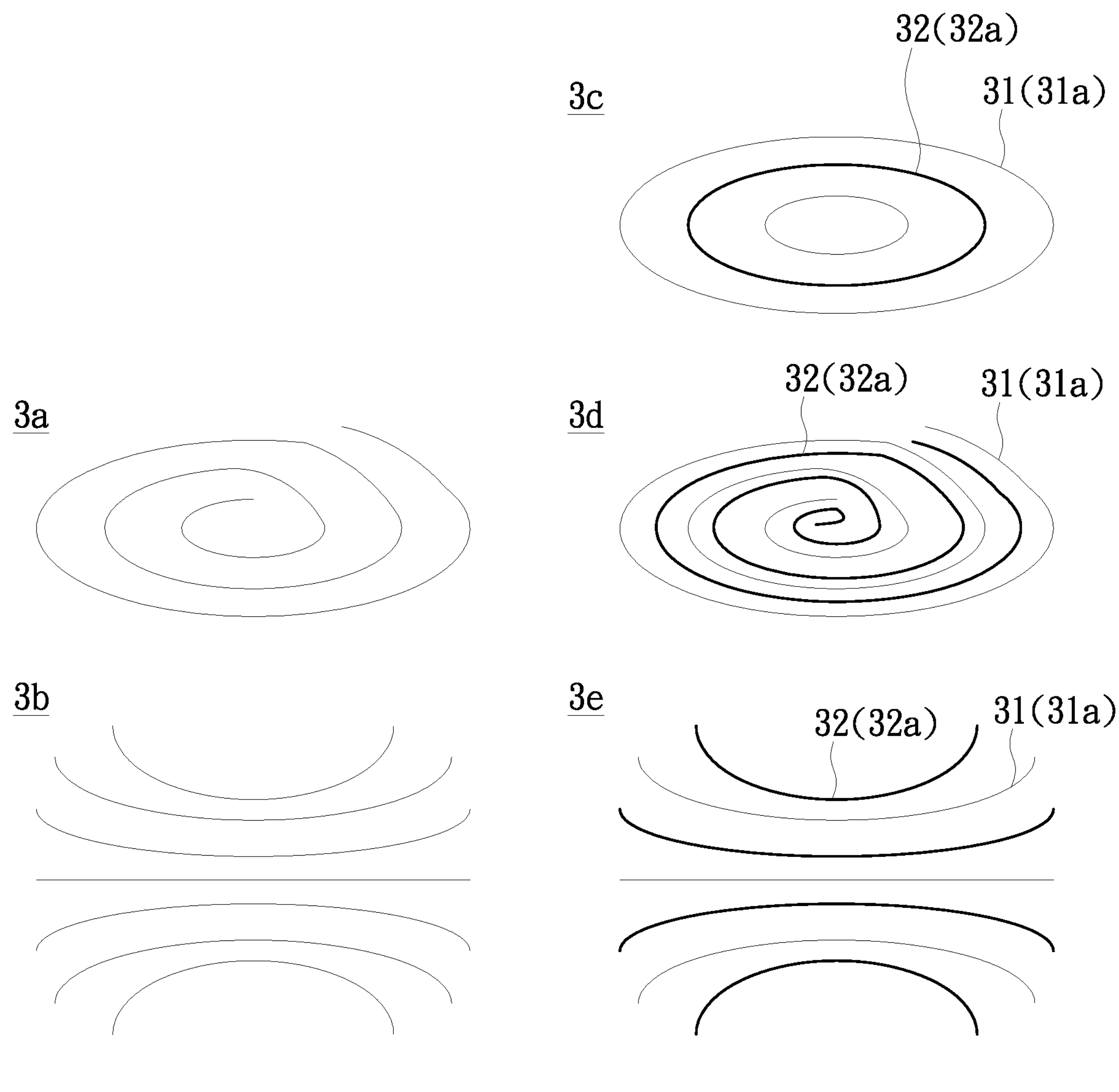
FIG. 4A is a schematic diagram of one type of discharge pattern in different embodiments of the present invention.
FIG. 4B is a schematic diagram of another type of discharge pattern in different embodiments of the present invention.

FIG. 4A is a schematic diagram of one type of discharge pattern in different embodiments of the present invention. Please refer to FIG. 2 and FIG. 4A. In the embodiment as shown in FIG. 2, the discharge pattern 3 is, for example, formed by printing with a coating, and the coating, for example, includes two metal particles having different redox potentials. The type and size of the metal particles in the coating, as well as the weight percentage of the metal particles in the coating, may be selected according to demands. The shape of the discharge pattern 3 is not limited. In different embodiments, the modality of the discharge pattern 3 may be, for example, a pattern formed by a plurality of ring-shaped graphics (such as discharge pattern 3 in FIG. 2), a pattern formed by spiral lines (such as discharge pattern 3*a* in FIG. 4A), or a pattern formed by a plurality of lines that do not contact with each other (such as discharge pattern 3*b* in FIG. 4A). The desired discharge pattern can be selected according to demands, such as the current intensity in a unit area or the direction of wrinkles. In addition, as the current intensity in a unit area is also affected by the number of metal particles in a unit area, the thickness of lines in the discharge pattern may also be changed according to demands.

FIG. 4B is a schematic diagram of another type of discharge pattern in different embodiments of the present invention. Please refer to FIG. 4B. In this type of embodiment, the discharge pattern 3*c*, the discharge pattern 3*d* and the discharge pattern 3*e* are separately provided with a first pattern portion 31 and a second pattern portion 32, where metals included in the first pattern portion 31 are different from metals included in the second pattern portion 32, and graphic lines in the first graphic portion 31 and graphic lines in the second graphic portion 32 are, for example, separated from each other. In some embodiments, the first pattern portion 31 and the second pattern portion 32 in FIG. 4B are formed by, for example, two types of printing coatings, and different printing coatings include metal particles having different redox potentials. Specifically, for example, one of the printing coatings only includes copper particles, while the other one of the metal coatings only includes zinc particles. In another type of embodiment, the first pattern portion 31 and the second pattern portion 32 may be formed by a first metal line 31*a* and a second metal line 32*a*, respectively, and the first metal line 31*a* and the second metal line 32*a* are two kinds of metal lines having different redox potentials.

As shown in FIG. 4B, in this type of embodiment, the first pattern portion 31 and the second pattern portion 32 may together form a pattern formed by a plurality of ring-shaped graphics (such as discharge pattern 3*c*), a pattern formed by two spiral lines (such as discharge pattern 3*d*), or a pattern formed by a plurality of lines that do not contact with each other (such as discharge pattern 3*e*). The desired modality can be selected according to demands, such as the current intensity in a unit area or the direction of wrinkles.

Figure 5:
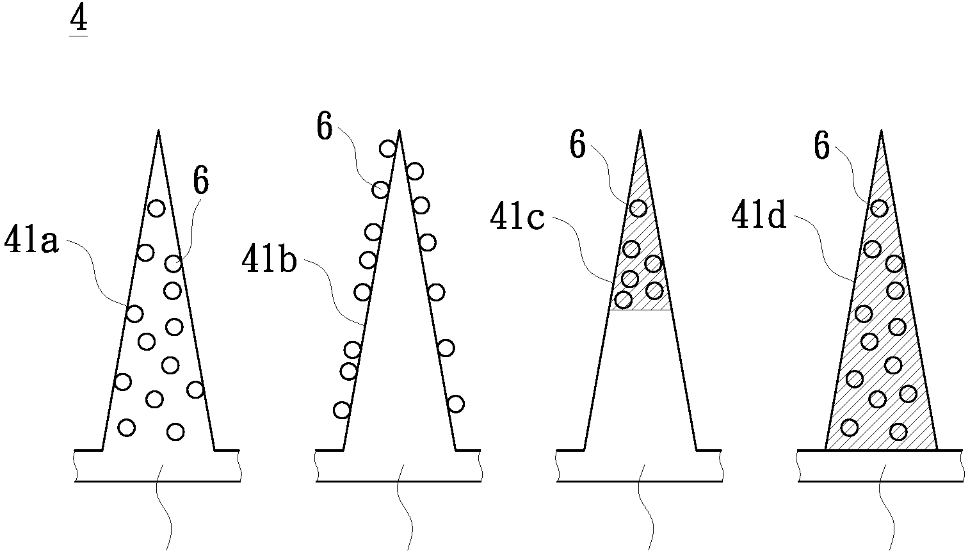
FIG. 5 is a schematic diagram of microneedle portions in different embodiments of the present invention.

FIG. 5 is a schematic diagram of microneedle portions in different embodiments of the present invention. In FIG. 5, portions drawn with section lines are soluble portions during use. The remaining portions are insoluble portions. As described above, the microneedle portion 4 is provided with conductive microneedles 41 capable of conducting electricity. In an embodiment where an electric current generated by the discharge pattern 3 can be conducted in the microneedle portion 4, the electric current can be conducted into the deep skin of a user through the conductive microneedles 41 of the microneedle portion 4, and accordingly, the effect of the electric current on promoting the absorption efficiency of ingredients in a liquid by the skin is improved.

In embodiments of the present invention, the conductive microneedles 41 on the microneedle portion 4 may be, depending on materials, one of insoluble microneedles (such as conductive microneedles 41*a* and conductive microneedles 41*b* in FIG. 5), soluble microneedles (such as conductive microneedles 41*d* in FIG. 5), or partially soluble microneedles (such as conductive microneedles 41*c* in FIG. 5). The length of the conductive microneedles 41 is, for example, less than 2,000 μm and may be set according to demands.

In an embodiment where the microneedle portion 4 is a microneedle patch capable of being separated from the flexible body 2 by assembly and disassembly, the microneedle patch may include a substrate sheet 42 and a plurality of conductive microneedles 41 connected to the substrate sheet 42. The substrate sheet 42 and the conductive microneedles 41 may be prepared from the same material or different materials. In an embodiment where the conductive microneedles 41*c* in FIG. 5 are provided, the conductive microneedles 41*c* may be prepared from a soluble material only at the tips of the microneedles and an insoluble material on other positions of the microneedles. In an embodiment where the conductive microneedles 41 are insoluble microneedles, the material is, for example, a conductive UV adhesive or a conductive polymer material. In an embodiment where the conductive microneedles 41 are soluble microneedles, the material is, for example, a sodium alginate mixture or other aqueous polymer materials. However, the material is not limited thereto.

When the microneedle patch is prepared from an aqueous material, the microneedle patch is, for example, manufactured separately from the flexible body 2 and then combined with the flexible body during use to prevent moisture in the microneedle patch from affecting the discharge pattern 3 on the flexible body 2 before use. When the microneedle patch is prepared from a non-aqueous material, the microneedle patch can be directly arranged on the flexible body 2 because the discharge of the discharge pattern 3 is not affected by the microneedle patch.

In some embodiments of the present invention, the conductive microneedles 41 of the microneedle portion 4 can be used as needle bodies for penetrating into the skin and conducting an electric current into the skin, and can also be used in cooperation with an additional drug 6. The drug 6 includes, for example, cosmetic ingredients intended to be absorbed by the human body, such as collagen, centella, ceramide, retinol, witch hazel, azelaic acid, hyaluronic acid, salicylic acid, vitamin C, niacin, vitamin B3, vitamin B5, sulfur, vitamin E powder, glycerol, GLP-1, insulin, acetaminophen or combinations thereof.

In different embodiments of the present invention, ingredients of the drug 6 may be the same or different from those contained in the liquid used in cooperation with the discharge pattern 3 in the preceding paragraph and may be selected according to demands.

In an embodiment where the microneedle portion 4 includes the insoluble conductive microneedles 41*a* as shown in FIG. 5, the drug 6 is, for example, mixed into the material of the conductive microneedles 41*a* during manufacturing, and the drug 6 on the surface may be released during use. However, the drug 6 in the conductive microneedles 41*a* is not released because the conductive microneedles 41*a* are not dissolved. In an embodiment where the microneedle portion 4 includes the insoluble conductive microneedles 41*b*, the material of the conductive microneedles 41*b* does not include the drug 6, and the drug 6 may be, for example, applied to the conductive microneedles 41*b* first and then used. In an embodiment where the microneedle portion 4 includes the soluble conductive microneedles 41*c* and the conductive microneedles 41*d*, the drug 6 is, for example, directly mixed into the material of the conductive microneedles 41*c* (in a soluble part) and the conductive microneedles 41*d* during manufacturing, so as to be absorbed directly by the skin of a user after dissolution.

In conclusion, as the compound facial mask of the present invention is provided with a discharge pattern and a microneedle portion at the same time, the absorption rate of active ingredients absorbed by the skin can be increased in two different ways including the discharge pattern for generating a micro-current acting on the skin and the microneedles for penetrating into the stratum corneum of the skin. Moreover, the conductive microneedle portion can be used as an electrode for penetrating into the skin to make an electric current conducted to the deeper skin, thereby achieving better effects. The problem that active ingredients of beauty liquids are not easily absorbed by the skin is solved.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A compound facial mask, comprising:

a flexible body;

a discharge pattern, positioned on a surface of the flexible body, wherein the discharge pattern comprises two metals, and the two metals have different redox potentials;

a microneedle portion, positioned on the surface, wherein the microneedle portion is prepared from a material different from the discharge pattern and provided with a plurality of conductive microneedles; and a conductive pattern, wherein the conductive pattern covers a surface on one side of the flexible body and is positioned between the flexible body and the discharge pattern.

2. The compound facial mask according to claim 1, wherein the discharge pattern is formed by printing with a coating, and the coating comprises two metal particles having different redox potentials.

3. The compound facial mask according to claim 1, wherein the discharge pattern is provided with a first pattern portion and a second pattern portion, the first pattern portion and the second pattern portion are separated from each other, and the first pattern portion and the second pattern portion comprise metal particles having different redox potentials.

4. The compound facial mask according to claim 1, wherein the discharge pattern comprises:

at least one first metal line, positioned on the flexible body to form a first metal pattern; and at least one second metal line, positioned on the flexible body to form a second metal pattern;

and the at least one second metal line and the at least one first metal line have different redox potentials and are interlaced and spaced with each other.

5. The compound facial mask according to claim 1, wherein the microneedle portion comprises a microneedle patch capable of being separated from the flexible body by assembly and disassembly.

6. The compound facial mask according to claim 1, wherein the conductive microneedles are soluble microneedles.

7. The compound facial mask according to claim 1, wherein the conductive microneedles are insoluble microneedles.

8. The compound facial mask according to claim 1, wherein the conductive microneedles comprise cosmetic ingredients.

9. The compound facial mask according to claim 1, wherein the surface is provided with at least one first area and at least one second area, the first area and the second area do not overlap, the microneedle portion is positioned in the first area, and the discharge pattern is positioned in the second area.

10. The compound facial mask according to claim 9, wherein the surface is further provided with a third area, the third area does not overlap with the first area and the second area, the microneedle portion and the discharge pattern are further positioned in the third area, and the discharge pattern is positioned between the microneedle portion and the flexible body.

11. The compound facial mask according to claim 1, wherein the material of the conductive pattern is a conductive fiber.

12. The compound facial mask according to claim 1, wherein the material of the conductive pattern is graphene ink.

* * * * *